United States Patent [19]

Chibata et al.

[11] 4,433,054

[45] Feb. 21, 1984

[54] ENZYMATIC ACTIVE SUBSTANCE IMMOBILIZED IN A POLYSACCHARIDE GEL MATRIX

[75] Inventors: Ichiro Chibata, Suita; Tetsuya Tosa, Kyoto; Isao Takata, Osaka, all of Japan

[73] Assignee: Tanabe Seiyaku Co., Ltd., Japan

[21] Appl. No.: 323,288

[22] Filed: Nov. 20, 1981

[30] Foreign Application Priority Data

Jan. 9, 1981 [JP] Japan ................................. 56-2410

[51] Int. Cl.³ .................... C12N 11/10; C12N 11/12; C12N 11/04
[52] U.S. Cl. .................................. 435/178; 435/179; 435/182
[58] Field of Search ............... 435/174, 177, 178, 182, 435/179

[56] References Cited

U.S. PATENT DOCUMENTS

| | | | |
|---|---|---|---|
| 4,138,292 | 2/1979 | Chibata et al. | 435/178 |
| 4,247,642 | 1/1981 | Hirohara et al. | 435/178 |
| 4,347,320 | 8/1982 | Borglum | 435/182 |

Primary Examiner—David M. Naff
Attorney, Agent, or Firm—Jordan B. Bierman; Linda Bierman

[57] ABSTRACT

An immobilized enzymatic active substance having an improved stability of enzymatic activity is prepared which comprises an enzymatic active substance such as microbial cells entrapped within a gel matrix of an unsubstituted amino, monoalkylamino or dialkylamino group-introduced polysaccharide having not less than 10 w/w % of sulfate moiety in the molecule thereof such as carrageenan. The immobilized enzymatic active substance is prepared by admixing the enzymatic active substance and an aqueous solution of the polysaccharide and then allowing to form a gel of the polysaccharide.

8 Claims, No Drawings

ENZYMATIC ACTIVE SUBSTANCE IMMOBILIZED IN A POLYSACCHARIDE GEL MATRIX

The present invention relates to a novel immobilized enzymatic active substance and a method for preparing the same.

Enzymatic reactions have been utilized in the production of various useful materials and in the decomposition of various undesirable materials or metabolites being harmful to human and livestock and, in order to carry out enzymatic reactions, efficiently, immobilized enzymatic active substances such as enzymes or microbial cells have been employed in the reactions.

Various methods have been known in the preparation of immobilized enzymatic active substances. In one of them, an enzymatic active substance is entrapped within a gel matrix of a polysaccharide such as agar or carrageenan by cooling an aqueous mixture of the substance and the polysaccharide to give an immobilized preparation. However, such an immobilized preparation has some disadvantages. For example, when the immobilized preparation obtained by using agar is employed in an enzymatic reaction at a high temperature, it is liable to lose its network structure and to be transformed into sol within a short period of time. When carrageenan is used, the gel matrix of the resulting preparation is unstable and it causes leakage of the enzymatic active substance from the preparation which results in lowing of enzymatic activity during the use of the preparation.

The present inventors have previously found that an immobilized enzymatic active substance having excellent properties without the above-mentioned disadvantages can be obtained by entrapping an enzymatic active substance within a gel matrix of a polysaccharide having not less than 10 w/w % of sulfate moiety ($-SO_3H$) in the molecule thereof under specific conditions and have filed patent applications directed to the immobilized substance and the method for preparing the same [U.S. Pat. No. 4,138,292 corresponding to Japanese Patent Publication (unexamined) No. 6483/1978].

As a result of the present inventor's further intensive study, it has been newly found that stability of enzymatic activity of the immobilized substance can be remarkably improved by using as the gel base thereof an amino or substituted amino group-introduced polysaccharide having no less than 10 w/w % of the sulfate moiety in the molecule thereof in stead of using the polysaccharide without introduction of amino group or a substituted amino group.

The main object of the present invention is to provide an immobilized enzymatic active substance having an improved stability of enzymatic activity and a method for preparing the same. This and other objects as well as advantages of the present invention will become apparent to those skilled in the art from the following description.

According to the present invention, there is provided an immobilized enzymatic active substance which comprises an enzymatic active substance and an amino or substituted amino group-introduced polysaccharide having not less than 10 w/w % of sulfate moiety in the molecule thereof and said substance being entrapped within a gel matrix of said polysaccharide.

The immobilized substance of the present invention can be prepared by admixing the enzymatic active substance and an aqueous solution of the polysaccharide and then allowing to form a gel of the polysaccharide in the mixture to entrap the substance within the resulting gel matrix.

The gel base used in the present invention is the polysaccharide having not less than 10 w/w %, generally, about 10 to 65 w/w % of sulfate moiety ($-SO_3H$) in the molecule thereof, into which amino group or a substituted amino group has been introduced. Examples of the polysaccharide having not less than 10 w/w % of the sulfate moiety in the molecule include carrageenan, furcellaran and cellulose sulfate. Carrageenan is a polysaccharide having 20 to 30 w/w % of the sulfate moiety which is obtained by refining an extract from sea weeds belonging to Rhodophyceae such as Gigartinaceae and Solievianceae. In the present invention, commercially available carrageenan, for example, "GENU GEL WG", "GENU GEL CWG" and "GENU VISCO J" (these are trade names of carrageenan manufactured by Kopenhagen Pectin Factory Ltd.) can be used. Furcellaran is a polysaccharide having 12 to 16 w/w % of the sulfate moiety which is obtained by extracting one kind of sea weeds belonging to Rhodophycease, that is, *Furcellaria fastigiata* and, for example, furcellaran manufactured by Litex Co. Denmark can be used. An examples of cellulose sulfate is "KELCO SCS" manufactured by Kelco Co.

The substituted amino group to be introduced into the polysaccharide having not less than 10 w/w % of the sulfate moiety in the molecule includes, for example, a monoalkylamino group having 1 to 12 carbon atoms in the alkyl moiety such as monomethylamino group, monoethylamino group, monopropylamino group or monobutylamino group; and a dialkylamino group having 1 to 12 carbon atoms in the alkyl moiety such as dimethylamino group, diethylamino group, dipropylamino group or dibutylamino group.

The amino group or substituted amino group can be introduced into the polysaccharide having not less than 10 w/w % of the sulfate moiety in the molecule, for example, by activating the polysaccharide with an epoxy compound (e.g. epichlorohydrin) or a cyanogen halide (e.g. cyanogen bromide) and reacting the activated polysaccharide with ammonium hydroxide, a monoalkylamine or a dialkylamine. In case of using an epoxy compound, the introduction is preferably carried out, for example, by reacting the polysaccharide with an epoxy compound at pH about 7 to 14 at 5° to 85° C. for about 10 minutes to 48 hours and then reacting the resulting activated polysaccharide with ammonium hydroxide, a monoalkylamine or a dialkylamine at pH about 7 to 14 at 5° to 85° C. for about 10 minutes to 72 hours. In case of using a cyanogen halide, the introduction is preferably carried out, for example, by adjusting pH of an aqueous solution of the polysaccharide to about 8 to 12, adding thereto an appropriate amount of a cyanogen halide, further adjusting pH of the resulting mixture to about 8 to 12 and then reacting the mixture with ammonium hydroxide, a monoalkylamine or a dialkylamine at about 5° to 30° C. for about 1 to 24 hours.

The content of amino group or the substituted amino group in the resulting amino or substituted amino group-introduced polysaccharide having not less than 10 w/w % of the sulfate moiety in the molecule is such that the amount of nitrogen per 1 g (dry weight) of the polysaccharide is 0.1 to 20 mg, preferably, 1 to 10 mg.

The enzymatic active substance used in the present invention may be enzymes, microbial cells and the like.

The enzymes used in the present invention are not specified and include, for example, oxido-reductases (e.g. amino acid oxidase, uricase, catalase, etc.), transferases (e.g. aspartate acetyltransferase, glycine aminotransferase, amino acid transferase, etc.), hydrolases (e.g. asparaginase, acetylcholine esterase, aminoacylase, etc.), lyases (e.g. fumarase, aspartate decarboxylase, aspartase, citrate lyase, etc.), isomerases (alanine racemase, glucose isomerase, glutamate racemase, etc.) and lygases (e.g. asparagine synthetase, glutathion synthetase, glutamine synthetase, etc.).

The microbial cells used in the present invention are not specified, either, so far as they can be used as enzyme sources. Examples of the microbial cells include those of bacteria, yeast, mold, lichens and protozoa containing the above-mentioned enzymes. The microbial cells may be living cells, freeze-dried cells or those obtained by freezing and thawing living cells, by treating living cells with acetone or by heating living cells.

The enzymatic active substance used in the present invention may be that of single enzyme system or a multiple enzyme system. Further, two or more enzymatic active substances may be used, simultaneously.

In carrying out the method for preparing the immobilized enzymatic active substance of the present invention, firstly, an aqueous solution of the amino or substituted amino group-introduced polysaccharide having not less than 10 w/w % of the sulfate moiety in the molecule is prepared. The preparation of the aqueous solution can be readily carried out by adding the polysaccharide to warm water at 30° to 90° C. The concentration of the polysaccharide in the solution is preferably 0.1 to 20 w/w %, preferably, about 1 to 10 w/w %. Then, the enzymatic active substance is added to the resulting aqueous solution of the polysaccharide to give a mixture. It is preferable to prepare the mixture by dissolving or suspending the enzymatic active substance in water, a physiological saline or an appropriate buffer solution (pH 1 to 13, preferably, 5 to 9) and mixing the resulting solution or suspension with the aqueous solution of the polysaccharide. The amount of the enzymatic active substance to be used depends upon the particular substance chosen, the particular substrate to be treated and the like, but, in general, the desired result can be obtained by using the substance in an amount of 0.001 to 50 g per 1 g of the polysaccharide.

Then, the polysaccharide in the above-obtained mixture is allowed to form a gel to entrap the enzymatic active substance within the resulting gel matrix of the polysaccharide. This gelation can be readily carried out by cooling the mixture of the polysaccharide and the enzymatic active substance. For example, when the mixture is allowed to stand at about 0° to 10° C. for about 30 minutes to 4 hours, the polysaccharide gels, and, simultaneously, the enzymatic active substance is entrapped within the resulting gel matrix of the polysaccharide. The gel thus obtained can be formed in an appropriate shape.

Besides, the gelation may be also carried out by contacting the mixture of the polysaccharide and the enzymatic active substance with a metal ion having an atomic weight of not less than 24 such as potassium ion, magnesium ion, calcium ion, aluminum ion and the like; by contacting the mixture with a compound having two or more basic functional groups in the molecule thereof such as methylenediamine, ethylenediamine, p-phenylenediamine and the like; or by contacting the mixture with a water-miscible organic solvent such as acetone, methanol, ethanol, propanol, dioxane, tetrahydrofuran, dimethyl sulfoxide and the like.

The immobilized enzymatic active substance of the present invention thus obtained can be used in various enzymatic reactions with substrates according to the same manner as that employed in conventional immobilized preparations. The immobilized preparation of the present invention shows an improved high level of enzymatic activity in comparison with conventional immobilized preparations since the enzymatic active substance hardly leaks out from the gel matrix of the polysaccharide when it is used in an enzymatic reaction. Further, since the immobilized enzymatic active substance of the present invention is superior to conventional immobilized preparations with respect to shape retention, strength, elasticity and the like, it can be stably used for a long period of time in an enzymatic reaction. Particularly, the immobilized enzymatic active substance of the present invention can fulfill its normal function without breakage of the gel structure even in the absence of a gel shape-retaining agent such as potassium ion since the gel-sol transformation temperature thereof become extremely high. Moreover, the immobilized enzymatic active substance of the present invention can be used even under such conditions that it is necessitated to carry out an enzymatic reaction in the presence of an organic solvent such as ethanol or acetone which denatures the enzymatic active substance since the stability of the immobilized preparation against the organic solvent is high. Furthermore, the immobilized enzymatic active substance of the present invention has a high stability against a protein denaturant such as urea, guanidine hydrochloride or the like. Furthermore, since the immobilized enzymatic active substance of the present invention has a high stability of enzymatic activity even at an elevated temperature, an enzymatic reaction can be carried at an elevated temperature and thereby the productivity of the desired product per unit time can be increased.

The following examples and experiments further illustrate the present invention in detail but are not to be construed to limit the scope thereof.

EXAMPLE 1

(1) Preparation of amino group-introduced carrageenan

GENU GEL WG (carrageenan manufactured by Kopenhagen Pectin Factory Ltd.) (5.0 g) was suspended in 1 N potassium hydroxide (50 ml). Epichlorohydrin (185 mg) was added to the resulting suspension and the mixture was shaken at 60° C. for 30 minutes. After cooling the reaction mixture to 5° C., cooled (5° C.) ethanol (50 ml) was added to the mixture. The resulting precipitate was filtered off and washed with cooled (5° C.) ethanol (20 ml×3) to give an epoxy-activated carrageenan. The epoxy-activated carrageenan was suspended in 0.9 M ammonium hydroxide (40 ml) and the suspension was shaken at 60° C. for 2 hours. Ethanol (50 ml) was added to the reaction mixture and the resulting precipitate was filtered off. The precipitate was washed with ethanol containing 0.1 N sodium hydroxide (20 ml×2) and ethanol (several times) to give an amino group-introduced carrageenan (4.3 g, dry weight).

(2) Preparation of immobilized *Brevibacterium flavum* cell preparation

*Brevibacterium flavum* ATCC 14067 was inoculated in a medium (pH 7.0, 500 ml) containing corn steep liquor (2.0%), malonic acid (2.0%), diammonium citrate (0.5%), monopotassium phosphate (0.2%) and magnesium sulfate heptahydrate (0.05%) and incubated with shaking at 30° C. for 48 hours. Then, the microbial cells were collected by centrifugation. The cells (8.0 g, wet weight) were suspended in a physiological saline (8 ml) and to the suspension was added 5% aqueous solution of the carrageenan obtained in the above (1) (34 ml) which was previously warmed to 50° C. The mixture was well stirred and allowed to stand at 4° C. for 30 minutes. The gel thus obtained was shaped into cubes of 3 mm in side length. The cubes were dipped in 1 M aqueous sodium fumarate solution (120 ml) containing 0.6% bile powder and allowed to stand at 37° C. for 24 hours. The cubes were washed with 2% aqueous potassium chloride solution to give an immobilized *Brevibacterium flavum* cell preparation having fumarase activity (50.0 g, wet weight).

1 M Aqueous sodium fumarate solution (pH 7.0, 40 ml) was added to the above-obtained immobilized *Brevibacterium flavum* cell preparation (6.35 g) and allowed to react at 37° C. with shaking. 15 and 30 minutes after the commencement of the reaction, each 1 ml sample of the reaction mixture was collected. Hydrochloric acid was added to the sample to precipitate unreacted fumaric acid and L-malic acid content of the resulting supernatant was determined colorimetrically by reacting it with 2,7-naphthalenediol. When fumarase activity was calculated based on an increase of the amount of L-malic acid in the reaction mixture during the 15 minute period, it was 1140 μmoles/hr/ml gel. This was corresponding to 63% of the enzymatic activity of the microbial cells used.

EXAMPLE 2

(1) Preparation of monoethylamino group-introduced carrageenan

According to the same procedure as described in Example 1 (1), the desired monoethylamino group-introduced carrageenan (4.0 g, dry weight) was obtained by using GENU GEL WG (carrageenan manufactured by Kopenhagen Pectin Factory Ltd.) (5.0 g), epichlorohydrin (247.5 mg) and monoethylamine (1.62 g).

(2) Preparation of immobilized *Brevibacterium flavum* cell preparation

The same procedure as described in Example 1 (2) was repeated except that 5% aqueous solution of the above-obtained monoethylamino group-introduced carrageenan (34 ml) was substituted for 5% aqueous solution of amino group-introduced carrageenan (34 ml) to give an immobilized *Brevibacterium flavum* cell preparation having fumarase activity (50.2 g, wet weight). Fumarase activity thereof was 909 μmoles/hr/ml gel and this was corresponding to 50% of the enzymatic activity of the microbial cells used.

EXAMPLE 3

(1) Preparation of diethylamino group-introduced carrageenan

According to the same procedure as described in Example 1 (1), the desired diethylamino group-introduced carrageenan (4.4 g, dry weight) was obtained by using GENU GEL WG (carrageenan manufactured by Kopenhagen Pectin Factory Ltd.) (5.0 g), epichlorohydrin (247.5 mg) and diethylamine (2.63 g).

(2) Preparation of immobilized *Brevibacterium flavum* cell preparation

The same procedure as described in Example 1 (2) was repeated except that 5% aqueous solution of the above-obtained diethylamino group-introduced carrageenan (34 ml) was substituted for 5% aqueous solution of amino group-introduced carrageenan (34 ml) to give an immobilized *Brevibacterium flavum* cell preparation having fumarase activity (50.3 g, wet weight). Fumarase activity thereof was 956 μmoles/hr/ml gel and this was corresponding to 53% of the enzymatic activity of the microbial cells used.

EXAMPLE 4

(1) Preparation of immobilized *Brevibacterium ammoniagenes* cell preparation

*Brevibacterium ammoniagenes* IAM 1645 was inoculated in a medium (pH 7.0, 500 ml) containing glucose (2.0%), fumaric acid (0.5%), urea (0.2%), monopotassium phosphate (0.2%), magnesium sulfate heptahydrate (0.05%) and corn steep liquor (1.0%) and incubated with shaking at 30° C. for 48 hours. Then, the microbial cells were collected by centrifugation. The cells (8.0 g, wet weight) were suspended in a physiological saline (8 ml) and to the suspension was added 5% aqueous solution of the monoethylamino group-introduced carrageenan obtained in Example 2 (1) (34 ml) which was previously warmed to 50° C. The mixture was well stirred and allowed to stand at 4° C. for 30 minutes. The gel thus obtained was shaped into cubes of 3 mm in side length. The cubes were washed with 2% aqueous potassium chloride solution to give an immobilized *Brevibacterium ammoniagenes* cells preparation having fumarase activity (50.0 g, wet weight). L-Malic acid productivity of the immobilized preparation was 525 μmoles/hr/ml gel and this was corresponding to 60% of the enzymatic activity of the microbial cells used.

EXPERIMENT 1

The following tests A to E were carried out by using the immobilized *Brevibacterium flavum* cell preparation obtained in Example 1 (2) (hereinafter referred to as Preparation A), the immobilized *Brevibacterium flavum* cell preparation obtained in Example 2 (2) (hereinafter referred to as Preparation B), the immobilized *Brevibacterium flavum* cell preparation obtained in Example 3 (2) (hereinafter referred to as Preparation C) and, as a control, an immobilized *Brevibacterium flavum* cell preparation obtained by using a carrageenan without introduction of amino group or a substituted amino group (hereinafter referred to as Preparation D).

Preparation D used as the control was prepared as follows:

The microbial cells obtained by the same procedure as described in Example 1 (2) (8.0 g, wet weight) was suspended in a physiological saline (8 ml) and to the suspension was added 5% aqueous solution of GENU GEL WG (carrageenan manufactured by Kopenhagen Pectin Factory Ltd.) (34ml) which was previously warmed to 50° C. The mixture was well stirred and allowed to stand at 4° C. for 30 minutes. The gel thus obtained was shaped into cubes of 3 mm in side length. The cubes were dipped in 1 M aqueous sodium fumarate solution (120 ml) containing 0.6% bile powder and allowed to stand at 37° C. for 24 hours. The cubes were washed with 2% of aqueous potassium chloride solution to give Preparation D (50.0 g, wet weight). When fumarase activity of Preparation D was determined according to the same procedure as described in Example 1 (2), it was 900 μmoles/hr/ml gel and this was corresponding to 49% of the enzymatic activity of the microbial cells used.

Test A

Stability in continuous enzymatic reaction

Preparations A to D were subjected to a continuous enzymatic reaction, respectively, by packing each preparation (6.3 g) in a column (1.6 cm×12 cm) with a jacket and continuously passing 1 M aqueous sodium fumarate solution (pH 7.0) through the column at 37° C. at the flow rate of 6 ml/hr over days and nights. The eluate was collected occasionally and fumarase activity of the preparation was determined according to the above-mentioned method. Further, the number of days required for the enzymatic activity of the preparation to be reduced to 50% of its initial activity (half-life) was calculated according to the following formula:

$$K_d = \frac{2.303}{t} \log \frac{n_0}{n} \quad t_{\frac{1}{2}} = \frac{0.693}{K_d}$$

wherein $K_d$ is deterioration rate constant (day$^{-1}$); t is reaction time (days); $n_0$ is initial enzymatic activity; n is enzymatic activity after t days; and $t_{\frac{1}{2}}$ is half-life (days).

The results are shown in Table 1.

TABLE 1

| Preparations Groups introduced into carrageenan | | A amino | The present invention B mono-ethyl-amino | C di-ethyl-amino | Control D non |
|---|---|---|---|---|---|
| Fumarase activity (μ moles/ hr/ml gel) | Continuous operation period (days) 1 | 1140 | 909 | 956 | 900 |
| | 9 | 1095 | 899 | 928 | 873 |
| | 15 | 1095 | 895 | 908 | 844 |
| | 21 | 1050 | 887 | 898 | 820 |
| | 30 | 1015 | 850 | 870 | 791 |
| | 42 | 969 | 828 | 833 | 745 |
| | 50 | 946 | 801 | 800 | 723 |
| | 64 | 901 | 780 | 771 | 674 |
| | 80 | 855 | 760 | 735 | 620 |
| | 100 | 798 | 712 | 692 | 584 |
| Half-life of fumarase activity (days) | | 194 | 241 | 216 | 160 |

Test B

Heat stability

Preparations A to D (each 2.0 g) were dipped in 0.1 M potassium phosphate buffer solution (pH 7.0, 2 ml), respectively, and heated at 60° C. for 15 hours. After heating, fumarase activity of each preparation was determined and the rate of residual fumarase activity thereof was calculated according to the following formula:

$$\text{Rate of residual fumarase activity (\%)} = \frac{\text{Fumarase activity after heating}}{\text{fumarase activity before heating}} \times 100$$

The results are shown in Table 2.

TABLE 2

| Preparations | | Group introduced into carrageenan | Rate of residual fumarase activity (%) |
|---|---|---|---|
| The present invention | A | amino | 30 |
| | B | monoethylamino | 47 |
| | C | diethylamino | 26 |
| Control | D | non | 12 |

Test C

Stability in solution of pH 4.5

Preparations A to D (each 2.0 g) were dipped in 0.5 M acetate buffer solution (pH 4.5, 5 ml), respectively, and allowed to stand at 37° C. for 1 hour. After treatment of the buffer solution, fumarase activity of each preparation was determined and the rate of residual fumarase activity thereof was calculated according to the following formula:

$$\text{Rate of residual fumarase activity (\%)} = \frac{\text{Fumarase activity after treatment with buffer solution}}{\text{Fumarase activity before treatment with buffer solution}} \times 100$$

The results are shown in Table 3.

TABLE 3

| Preparations | | Group introduced into carrageenan | Rate of residual fumarase activity (%) |
|---|---|---|---|
| The present invention | A | amino | 100 |
| | B | monoethylamino | 93 |
| | C | diethylamino | 83 |
| Control | D | non | 3 |

Test D

Stability in ethanol-containing solution

Preparations A to D (each 2.0 g) were dipped in 2% aqueous potassium chloride solution (2.0 ml) containing ethanol (0.46 g), respectively, and allowed to stand at 37° C. for 30 minutes. After treatment with the ethanol-containing solution, fumarase activity of each preparation was determined and the rate of residual fumarase activity thereof was calculated according to the following formula:

$$\text{Rate of residual fumarase activity (\%)} = \frac{\text{Fumarase activity after treatment with ethanol-containing solution}}{\text{Fumarase activity before treatment with ethanol-containing solution}} \times 100$$

The results are shown in Table 4.

TABLE 4

| Preparations | | Group introduced into carrageenan | Rate of residual fumarase activity (%) |
|---|---|---|---|
| The present | A | amino | 88 |

TABLE 4-continued

| Preparations | | Group introduced into carrageenan | Rate of residual fumarase activity (%) |
|---|---|---|---|
| invention | B | monoethylamino | 83 |
| | C | diethylamino | 85 |
| Control | D | non | 73 |

Test E

Stability in urea-containing solution

Preparations A to D (each 2.0 g) were dipped in 2% aqueous potassium chloride solution (2.0 ml) containing urea (0.36 g), respectively, and allowed to stand at 37° C. for 30 minutes. After treatment with the urea-containing solution, fumarase activity of each preparation was determined and the rate of residual fumarase activity thereof was calculated according to the following formula:

$$\text{Rate of residual fumarase activity (\%)} = \frac{\text{Fumarase activity after treatment with urea-containing solution}}{\text{Fumarase activity before treatment with urea-containing solution}} \times 100$$

The results are shown in Table 5.

TABLE 5

| Preparations | | Group introduced into carrageenan | Rate of residual fumarase activity (%) |
|---|---|---|---|
| The present invention | A | amino | 70 |
| | B | monoethylamino | 93 |
| | C | diethylamino | 65 |
| Control | D | non | 56 |

EXPERIMENT 2

The following tests F to I were carried out by using the immobilized *Brevibacterium ammoniagenes* cell preparation obtained in Example 4 (1) (hereinafter referred to as Preparation E) and, as a control, an immobilized *Brevibacterium ammoniagenes* cell preparation obtained by using a carrageenan without introduction of amino group or a substituted amino group (hereinafter referred to as Preparation F).

Preparation F used as the control was prepared as follows:

The microbial cells obtained by the same procedure as described in Example 4 (1) (8.0 g, wet weight) was suspended in a physiological saline (8 ml) and worked up according to the same procedure as that of Preparation D in Experiment 1 to give Preparation F (49.7 g, wet weight). L-Malic acid productivity of Preparation F was 509 μmoles/hr/ml gel and this was corresponding to 58% of the enzymatic activity of the microbial cells used.

Test F

Stability in continuous enzymatic reaction

According to the same procedure as described in Experiment 1, Test A, Preparations E and F (each 6.3 g) were subjected to a continuous enzymatic reaction, respectively. Fumarase activity and half-life of each preparation were determined as in Experiment 1, Test A. The results are shown in Table 6.

TABLE 6

| Preparations Group introduced into carrageenan | | | The present invention E monoethylamino | Control F non |
|---|---|---|---|---|
| Fumarase activity (μ moles/ hr/ml gel) | Continuous operation period (days) | 1 | 525 | 509 |
| | | 9 | 499 | 477 |
| | | 15 | 478 | 441 |
| | | 21 | 458 | 418 |
| | | 30 | 437 | 383 |
| | | 42 | 410 | 344 |
| | | 50 | 401 | 308 |
| | | 64 | 366 | 266 |
| | | 80 | 341 | 231 |
| | | 100 | 303 | 198 |
| Half-life of fumarase activity (days) | | | 127 | 75 |

Test G

Stability in solution of pH 4.5

Preparations E and F (each 2.0 g) were dipped in 0.5 M acetate buffer solution (pH 4.5, 5 ml), respectively, and allowed to stand at 37° C. for 1 hour. After treatment of the buffer solution, fumarase activity of each preparation was determined and the rate of residual fumarase activity thereof was calculated according to the same formula as in Experiment 1, Test C. The results are shown in Table 7.

TABLE 7

| Preparations | | Group introduced into carrageenan | Rate of residual fumarase activity (%) |
|---|---|---|---|
| The present invention | E | monoethylamino | 47 |
| Control | F | non | 12 |

Test H

Stability in ethanol-containing solution

Preparations E and F (each 2.0 g) were dipped in 2% aqueous potassium chloride solution (2.0 ml) containing ethanol (0.46 g), respectively, and allowed to stand at 37° C. for 30 minutes. After treatment with the ethanol-containing solution, fumarase activity of each preparation was determined and the rate of residual fumarase activity thereof was calculated according to the same formula as in Experiment 1, Test D. The results are shown in Table 8.

TABLE 8

| Preparations | | Group introduced into carrageenan | Rate of residual fumarase activity (%) |
|---|---|---|---|
| The present invention | E | monoethylamino | 28 |
| Control | F | non | 3 |

Test I

Stability in urea-containing solution

Preparations E and F (each 2.0 g) were dipped in 2% aqueous potassium chloride solution (2.0 ml) containing urea (0.36 g) and allowed to stand at 37° C. for 30 minutes. After treatment with the urea-containing solution, fumarase activity of each preparation was determined and the rate of residual fumarase activity thereof was calculated according to the same formula as in Experiment 1, Test E. The results are shown in Table 9.

TABLE 9

| Preparations | | Group introduced into carrageenan | Rate of residual fumarase activity (%) |
|---|---|---|---|
| The present invention | E | monoethylamino | 81 |
| Control | F | non | 13 |

What is claimed is:

1. An immobilized enzymatic active substance which comprises an enzymatic active substance and an unsubstituted amino, monoalkylamino or dialkylamino group-introduced carrageenan wherein said group is present in said carrageenan in an amount such that there is 0.1 to 20 mg of nitrogen present per 1 g of dry weight of said carrageenan and each alkyl is individually 1 to 12 carbon atoms, said enzymatic active substance being entrapped within a gel matrix of said carrageenan.

2. The immobilized enzymatic active substance according to claim 1, wherein said enzymatic active substance is microbial cells.

3. The immobilized enzymatic active substance according to claim 2, wherein said carrageenan is amino group-introduced carrageenan, monoethylamino group-introduced carrageenan or diethylamino group-introduced carrageenan.

4. A method for preparing an immobilized enzymatic active substance which comprises admixing an enzymatic active substance and an aqueous solution of an unsubstituted amino, monoalkylamino or dialkylamino group-introduced carrageenan wherein said group is present in an amount such that there is 0.1 to 20 mg of nitrogen present per 1 g dry weight of said carrageenan and each alkyl is individually 1 to 12 carbon atoms, and then gelling said carrageenan to entrap said enzymatic active substance within the resulting gel matrix.

5. The method according to claim 4, wherein said aqueous solution of the carrageenan is prepared by adding a sufficient amount of carrageenan to warm water at 30° to 90° C. to form a solution containing 0.1 to 20 w/w % of the carrageenan.

6. The method according to claim 4, wherein said enzymatic active substance is dissolved or suspended in water, a physiological saline, or a buffer solution and then mixed with said aqueous solution of carrageenan.

7. The method according to claim 4, wherein said gelling is carried out by allowing said mixture of said enzymatic active substance and said carrageenan to stand at about 0° to 10° C. for about 30 minutes to about 4 hours.

8. The method according to claim 4, 5, 6 or 7, wherein said enzymatic active substance is microbial cells.

* * * * *